United States Patent [19]

Yano et al.

[11] Patent Number: 5,604,120
[45] Date of Patent: Feb. 18, 1997

[54] METHOD FOR PRODUCING OPTICALLY ACTIVE ENDO-2-NORBORNEOLS

[75] Inventors: Hitoshi Yano; Teruyo Sugiura; Yasuyuki Koizumi; Naoyuki Yoshida, all of Ichihara, Japan

[73] Assignee: Chisso Corporation, Tokyo, Japan

[21] Appl. No.: 517,792

[22] Filed: Aug. 22, 1995

[30] Foreign Application Priority Data

Aug. 22, 1994 [JP] Japan ..................... 6-218324

[51] Int. Cl.$^6$ ................. C12P 7/62; C12P 7/02
[52] U.S. Cl. ............. 435/135; 435/155; 435/197; 435/198; 435/280
[58] Field of Search ................. 435/155, 280, 435/135, 197, 198

[56] References Cited

U.S. PATENT DOCUMENTS

| | | | |
|---|---|---|---|
| 5,270,206 | 12/1993 | Saccomano | 435/280 |
| 5,407,828 | 4/1995 | Kierkels et al. | 435/280 |
| 5,459,067 | 10/1995 | Kageyama et al. | 435/280 |

OTHER PUBLICATIONS

Brackenridge et al. J Chem Soc. Perkin Trans 1 (1993) 1093–1094 "Enzymatic Resolution of Oxalate Esters of a Tertiary Alchol Using Porcing Pancreatic Lipase".

*Primary Examiner*—Herbert J. Lilling
*Attorney, Agent, or Firm*—Wenderoth, Lind & Ponack

[57] ABSTRACT

The present invention provides a method for producing optically active endo-2-norborneols, represented by the following formula:

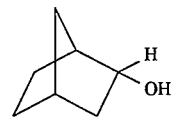

and the antipodes, it comprises asymmetrically hydrolysing racemic endo-2-acyloxynorbornane or endo-2-acyloxynorbornane, whose (R)-compound is in excess, having an optical purity of 50–95% ee with lipase derived from Candida genus. The optically active endo-2-norborneol useful for synthesizing intermediates of pharmaceutical preparations in large quantities.

12 Claims, No Drawings

METHOD FOR PRODUCING OPTICALLY ACTIVE ENDO-2-NORBORNEOLS

BACKGROUND OF THE INVENTION

The present invention relates to a method for producing efficiently optically active endo-2-norborneols useful as synthetic intermediates of pharmaceutical preparations and the like.

In recent years, it has been earnestly required to synthesize physiological active materials of pharmaceutical preparations as optically active compounds. When these materials have optical isomers, several isomers have different active properties. One isomer exhibits strong activity and the other isomer exhibits little activity or exhibits undesirable toxicity. When physiologically active materials are synthesized for pharmaceutical preparations, therefore, it is desired to selectively prepare optical isomers having preferable steric configuration in view of a fully developed physiological activity and safety.

Hitherto, to obtain optically active endo-2-norborneols, the following methods have been reported: (1) a method for optically resolving racemic endo-2-norborneols by a diastereomer method (Winstein et al., J. Am. Chem. Soc., 74, 1147 (1952)), (2) a method for optically resolving racemic 2-norbornanone with a microorganism by stereoselective reduction (Nakazaki et al., J. Org. Chem., 45, 4432 (1980)), (3) a method for stereoselectively reducing racemic 2-norbornanone with alcohol dehydrogenase of horse liver (Jones et al., J. Am. Chem. Soc., 98, 8476 (1976)), (4) a method for stereoselectively acylating racemic endo-2-norborneol in the presence of lipase of pig spleen (Saccomano et al., Tetrahedron Lett., 33, 1201 (1992)), (5) a method of stereoselective transesterification of racemic endo-2-acetoxynorbornane in the presence of the lipase derived from Candida cylindracea (Macfarlane et al., J. Chem. Soc. Perkin. Trans., 1, 2287 (1993)), (6) a method for stereoselectively acylating racemic-endo-2-norborneol in the presence of lipase derived from Pseudomonas (Naemura et al., Bull. Chem. Soc. Jpn., 66, 573 (1993)), (7) a method for stereoselectively hydrolyzing racemic endo-2-acetoxynorbornane in the presence of the lipase derived from *Candida cylindracea* (Brackenridge et al., J. Chem. Soc. Perkin. Trans., 1, 1093 (1993) and the like.

The method of (1) however is not efficient because recrystallization should be repeated to increase the optical purities of the resulting compounds. In the method of (2), further, it is difficult to obtain strains to be used and the substrate concentration is very low against much charge stock (0.075 w/v %). The method of (3) is impractical because it is difficult to obtain alcohol dehydrogenase and NAD of a coenzyme, and the yield is low in the asymmetric reaction. In the method of (4), a side reaction easily occurs and the water content of the reaction system should be decreased precisely to prevent the side reaction. Since the enzyme should be added several times during the reaction, the operation is very troublesome. The method is industrially disadvantageous because diethylether, which is very flammable as a reaction solvent, should be used. In the method of (5), it is difficult to obtain the ester of starting materials and the low optical purity of the product is insufficiently 32% ee. In the method of (6), the optical purity of the product is also very low and it is 63%. The water content of the reaction system should be decreased to prevent the side reaction. The stability of isopropenyl acetate of an acylation agent is not enough and it is difficult to obtain the compound in large quantities. Although the method of (7) is very close to the method of the present invention, it does not disclose enough the reaction conditions and the optical purity of the product is very low 60% ee.

These conventional methods have been not perfect in practical use at the industrial level.

SUMMARY OF THE INVENTION

The present invention aims to overcome the problems of said conventional methods and to provide a method for efficiently producing in high optical purities and in large quantities optically active endo-2-norborneol of intermediates useful for synthesizing pharmaceutical preparations by a simple process.

The present invention has the following features to overcome the above problems.

One of the features is a method for producing optically active endo-2-norborneols, characterized in that it comprises asymmetrically hydrolysing racemic endo-2-acyloxynorbornane represented by formula (1):

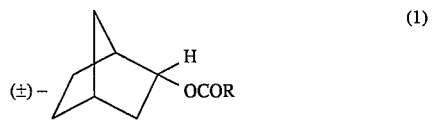

(wherein R is straight or branched alkyl of 1–22 carbon atoms, alkenyl of 1–22 carbon atoms, cycloalkyl, aralkyl or aryl group) with lipase derived from Candida genus, obtaining a mixture of (R)-endo-2-norborneol represented by formula (2):

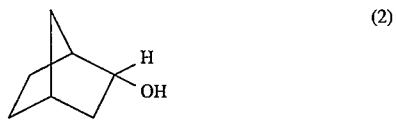

and (S)-endo-2-acyloxynorbornane represented by formula (3):

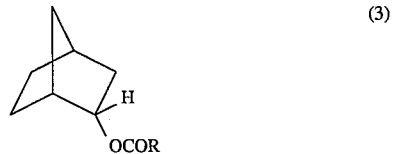

and isolating these compounds.

Preferably, above (S)-endo-2-acyloxynorbornane represented by formula (3) is further hydrolyzed under acidic or basic conditions to obtain (S)-endo-2-norborneol represented by formula (4):

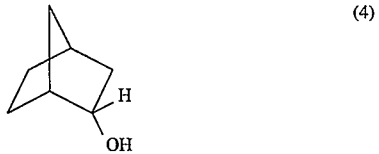

Another is a method for producing (R)-endo-2-norborneol having an optical purity of more than 95% ee and represented by formula (2):

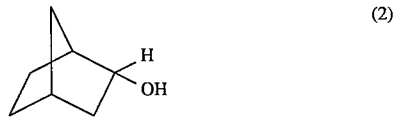

by asymmetrically hydrolyzing endo-2-acyloxynorbornane whose (R)-compound is in excess, having an optical purity of 50–95% ee and represented by formula (5):

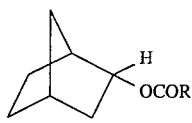

wherein R is straight or branched alkyl of 1–22 carbon atoms, alkenyl of 1–22 carbon atoms, cycloalkyl, aralkyl or aryl group with lipase derived from Candida genus. By using this method, (R)-endo-2-norborneol having a high purity can be obtained.

DETAILED DESCRIPTION OF THE INVENTION

The above mentioned lipase is preferably derived from *Candida antarctica*.

The lipase is preferably immobilized on a carrier.

When the lipase is immobilized on the carrier, further, lipase derived from *Candida antarctica* is preferred.

As the carrier for immobilizing the lipase, it is selected from the group consisting of porous polypropylene, porous acryl resin, polysaccharide gel modified with a formyl or epoxy group on the surface, acryl resin modified with a formyl or epoxy group on the surface, and polymer gel of a silicone type modified with a formyl or epoxy group.

In the production method of the present invention, racemic endo-2-acyloxynorbornane represented by formula (1) or endo-2-acyloxynorbornane represented by formula (5) having (R)-compound in excess and having an optical purity of 50–95% ee is used as the starting material, and R in the formula is selected from straight or branched alkyl of 1–22 carbon atoms, alkenyl of 1–22 carbon atoms, cycloalkyl, aralkyl or aryl group. Most preferably, methyl, ethyl, n-propyl, n-butyl and n-pentyl can be exemplified as straight alkyl groups; i-propyl, sec-butyl, t-butyl and neopentyl can be exemplified as the branched alkyl groups; vinyl and 2-methyl vinyl can be exemplified as the alkenyl groups; and cyclohexyl as the cycloalkyl group, phenyl as the aryl group and benzyl as the aralkyl can be exemplified, respectively. Most preferable ones are ethyl, n-pentyl or benzyl.

The said racemic endo-2-acyloxynorbornane represented by formula (1) can be obtained by acylation of racemic endo-2-norbornanol by using a well-known acylation method, for example, in the presence of a base such as pyridine in a nonprotonic solvent with acyl chloride.

The endo-2-acyloxynorbornane represented by formula (5) can be, further, obtained by a well-known acylation method: acylation of endo-2-norbornanol, which has an optical purity of 50–95% ee and (R)-compound in excess, with acyl chloride in nonprotic solvent in the presence of a base such as pyridine, or stereoselectively acylation of racemic endo-2-norbornanol in the presence of lipase (for example, Saccomano et al., Tetrahedron Lett., 33, 1201 (1992)).

The production method of the present invention is conducted by mixing with stirring racemic endo-2-acyloxynorbornane represented by formula (1) or endo-2-acyloxynorbornane represented by formula (5) with lipase in a solvent for hydrolyzing reaction.

The reaction temperature for hydrolyzing the compound is suitably from 0° C. to 100° C. in general, preferably from 10° C. to 50° C. If the reaction temperature is 0° C. and below, it becomes difficult for the reaction to proceed. If it is 100° C. and over, a deactivation phenomenon of the lipase appears and the reaction is undesirably retarded.

The reaction time is suitably one to 1000 hours in general, preferably one to 200 hours. The reaction time may be changed by the kind of substrates and the reaction temperature. If the reaction time is too short, the conversion may be insufficient. If the reaction time is too long, it is undesired from the reaction efficiency.

The amount of lipase is suitably 0.1 to 500% by weight of the substrate in general, preferably one to 100% by weight. If the amount is 0.1% by weight and below, it is difficult for the reaction to proceed. If the amount is 500% and over, the stirring operation becomes difficult by increasing the viscosity of the reaction liquid. In addition to operation problems such as difficulty of isolation of the object products, the lipase is used too much to catalyze the reaction, and such problems are economically undesirable.

As the kind of lipase, the lipase derived from Candida is suitable for catalyzing the hydrolytic reaction to act on racemic endo-2-acyloxynorbornane, and the lipase derived from *Candida antarctica* is more preferred. An embodiment, the lipase commercially available in the trade name of Novozym 435 or SP 525 (both are manufactured by Novo Nordisc) can be exemplified.

After using the lipase, the lipase may be used again. For such reuse, immobilized lipase is efficiently used.

Immobilized lipase commercially available is used as it is, or lipase not immobilized can be used after it is immobilized by the following method. Namely, the latter lipase is dispersed in ion exchange water, distilled water or a buffer solution and then a carrier is added. When the carrier is an adsorption type, the lipase is adsorbed and immobilized on it. When the carrier is a covalent linkage type, the lipase is reacted with a functional group on the carrier, if necessary, stabilized by a method such as reduction of the reaction part, and immobilized on the carrier.

As the above carrier, powder or granules of polymer materials such as polypropylene, acryl resins, polysaccharide gel or silicone resin can be exemplified. The carrier of an adsorption type may have multi-cellular structure, and the carrier of a covalent bond type may have the surface activated with cyanogen bromide or modified with formyl, epoxy, carboxyl, amino or the like.

The carrier of an adsorption type, especially, may be preferably produced with polymer materials such as polypropylene and acryl resins. The carrier of a covalent bond type, particularly, acryl resin, polysaccharide gel and silicone resin having the surface modified with formyl or epoxy can be preferably obtained. An embodiment of the polysaccharide gel modified with formyl is Formyl-cellulofine (Trade name, manufactured by CHISSO CORPORATION).

After the hydrolysis reaction, the immobilized lipase is recovered by filtration, decantation or the like from the reaction system and the lipase may be used as it is in the next reaction.

Ion exchange water, distilled water or buffer solution is suitably used as solvent. An organic solvent miscible with the above solvent such as acetone, N,N-dimethylformamide, dimethylsulfoxide and alcohol can be used as compatible solvent. The amount of the solvent is 0.1 to 100 times by weight of racemic endo-2-acyloxynorbornane (1) which is a substrate, preferably one to 10 times by weight when the reaction efficiency is considered.

Since organic acids are liberated from the mixture with the reaction, it is necessary to maintain an optimum pH of lipase in the reaction system. For that purpose, a buffer solution adjusted to optimum pH may be used, or the optimum pH in the system may be maintained by dropping a solution of sodium hydroxide.

After the hydrolysis reaction, the resulting mixture of (R)-endo-2-norborneol and (S)-endo-2-acyloxynorbornane is extracted with organic solvent, the extract solution is concentrated, and the concentrate is treated by distillation or column chromatography to isolate (R)-endo-2-norborneol and (S)-endo-2-acyloxynorbornane, respectively. The resulting (S)-endo-2-acyloxynorbornane is treated by hydrolysis under acidic or basic conditions to obtain optically active (S)-endo-2-norborneol.

The optically active endo-2-norborneol obtained in the present invention is useful as an intermediate for synthesizing medical supplies.

The resulting (R)-(+)-endo-2-norborneol (2) can be led, for example, via the following steps to a pyrimidone derivative (9) useful as medicines for treating asthma, bronchitis, dermatitis and the like.

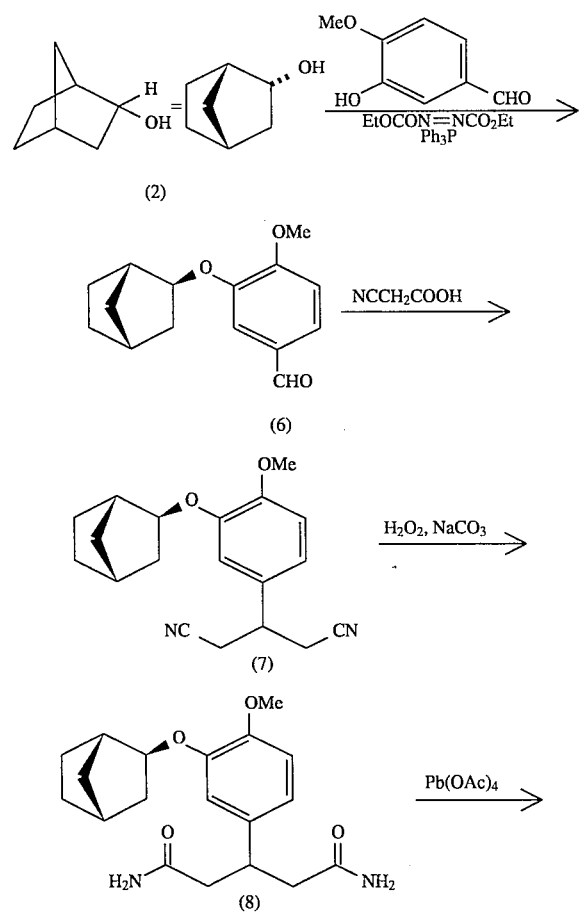

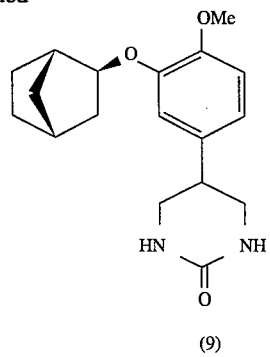

Namely, (R)-(+)-endo-2-norborneol (2) in tetrahydrofuran is reacted under reflux with 3-hydroxy-4-methoxybenzaldehyde in the presence of diethyl azodicarboxlate and triphenyl phosphine to obtain 3-[(2S)-exo-bicyclo[2.2.1]hepto-2-yloxy]-4-methoxybenzaldehyde (6), then via three steps (as shown in EPO 428 313 A), and the pyrimidone derivative (9) is derived.

The above-mentioned (R)-(+)-endo-2-norborneol (2) can be led to thromboxane A2 receptor anthagonist (14) useful for an anticoagulant via the following steps.

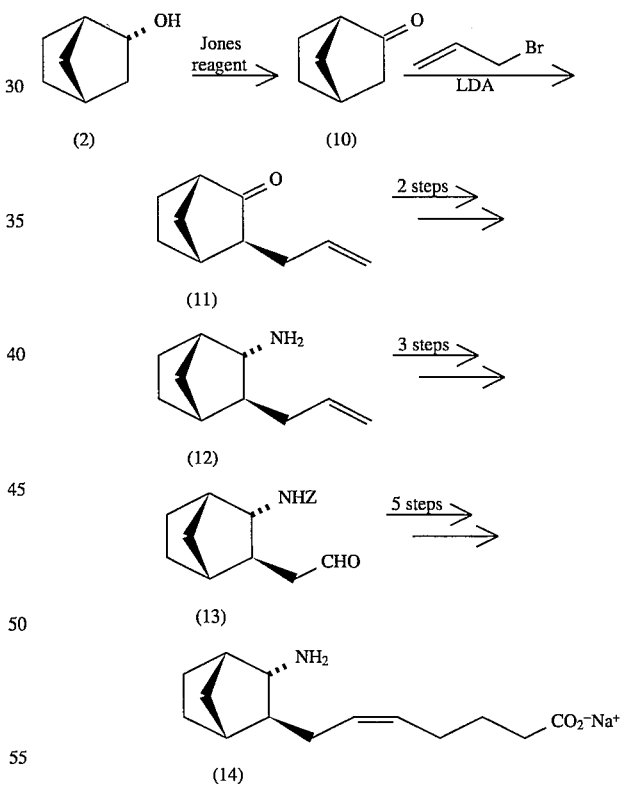

(R)-(+)-endo-2-norborneol (2) in acetone is reacted with a Jones reagent previously prepared from sulfuric acid and chromium trioxide under cooling conditions to obtain (R)-(+)-2-norbornanone (10), then via several steps (as shown in a method of Narisada et al., J. Med. Chem., 31, 1847

(1988)), and the desired thromboxane A2 receptor anthagonist (14) is derived.

The advantages of the invention are as follows:
(1) Optically active endo-2-norborneol can be obtained at high optical purities (more than 76% ee).
(2) When the lipase is immobilized, it can be recovered and reused.
(3) The production method of the present invention is based on hydrolysis reaction so that it can be conducted in an open system without considering contamination of moisture.
(4) The reaction process can be conducted at moderate temperatures (about room temperature).

DESCRIPTION OF PREFERRED EMBODIMENTS

The following examples and comparative examples illustrate the present invention more specifically, but these will not always be precise in practical applications.

Optical purities of optically active endo-2-norborneol in these examples are determined by analysis of capillary gas chromatography (Trade name: β-DEX (Trademark) 120; manufactured by Sperco).

EXAMPLE 1

Racemic endo-2-propionyloxy norbornane 1.7 g (10 mmol), lipase (SP 435, origin: *Candida antarctica*, manufactured by Navo Nordisc Company) 0.25 g and a 0.7M phosphoric buffer solution (pH 7.0) 30 ml were mixed with stirring for 160 hours at 35° C. Then, the conversion of the racemic compound was 37%. The lipase was filtered from the reaction solution. The filtrate was extracted with ethyl acetate, the extract was dried over magnesium sulfate and the solvent was distilled off under reduced pressure. The residue was subjected to a chromatograph over silica gel to obtain (R)-endo-2-norborneol (0.39 mg, 3.5 mmol, 35%). After the compound was subjected to the said chromatograph, the optical purity was 93% ee.

EXAMPLE 2

The same procedure as in Example 1 was repeated and a mixture was prepared except that SP 525 (origin: *Candida antarctica*, manufactured by Novo Nordisc Company) was used instead of Novozym 435, and the mixture was stirred for 110 hours. Then, the conversion was 47%. The same steps as in Example 1 were conducted from the filtration of the lipase to the chromatography of the product to obtain (R)-endo-2-norborneol (0.50 g, 4.3 mmol, 43%). After the compound was subjected to the said chromatograph, the optical purity was 88% ee.

EXAMPLE 3

Racetalc endo-2-norbornane phenyl acetate 2.3 g (10 mmol), lipase (Trade name: type VII, origin: *Candida cylindracea*, manufactured by Sigma Company) 0.25 g and a 0.7M phosphoric buffer solution (pH 7.0) 30 ml were mixed with stirring for 264 hours at 35° C. Then, the conversion of the racemic compound was 16%. The lipase was filtered off. The filtrate was extracted with ethyl acetate, the extract was dried over magnesium sulfate and the solvent was distilled off under reduced pressure. The residue was subjected to a chromatograph over silica gel to obtain (R)-endo-2-norborneol (0.1 3 g, 1.2 mmol, 12%). After the compound was subjected to the said chromatograph, the optical purity was 82% ee.

EXAMPLE 4

The same procedure as in Example 3 was repeated and a mixture was prepared except that racemic endo-2-propionyloxy norbornane 1.7 g (10 mmol) was used instead of racemic endo-2-norbornyl phenylacetate 2.3 g (10 mmol) as a substrate, and the mixture was stirred for 29 hours. Then, the conversion was 67%. The same steps as in Example 3 were conducted from the filtration of the lipase to the chromatography of the product to obtain (S)-endo-2-propionyloxy norbornane (0.51 g, 3.0 mmol, 30%). The resulting compound was dissolved in ethanol 10 ml, and 1N sodium hydroxide 10 ml was added to it and stirred for one night at room temperature. The reaction solution obtained was neutralized with 1N hydrochloric acid and extracted with ethyl acetate, the extract was dried over magnesium sulfate, and the solvent was distilled off under reduced pressure to obtain (S)-endo-2-norborneol (0.17 g, 2.6 mmol, 26%). After the compound was subjected to the said chromatograph, the optical purity was 76% ee.

Comparative examples 1–8

Several kinds of enzymes 0.25 g as shown in Table 1, respectively, are mixed with racemic endo-2-propionyloxy norbornane 1.7 g (10 mmol) and a 0.7M phosphoric buffer solution (pH 7.0) 30 ml, and the mixture was stirred at 35° C. for the fixed time. The results are shown in Table 1.

TABLE 1

| Comparative example | Enzyme (Trade name) | Stirring (hr.) | Conversion (%) | Optical purity (% ee) |
|---|---|---|---|---|
| 1 | Pancreatic trypsin[1] | 94 | 0.3 | — |
| 2 | Lecitase[2] | 67 | 0 | — |
| 3 | Paratase A[3] | 95 | 0 | — |
| 4 | SP 523[4] | 142 | 45 | 50 |
| 5 | Lipase type II[5] | 70 | 1.0 | — |
| 6 | Protease type I[6] | 43 | 0 | — |
| 7 | Liver acetone powder[7] | 77 | 42 | 15 |
| 8 | Pancreatin F[8] | 94 | 0.3 | — |

[1] Origin: Porcin pancreas, manufactured by Novo Nordisc Co., Ltd.
[2] Origin: Porcin pancreas, manufactured by Novo Nordisc Co., Ltd.
[3] Origin: Aspergillus niger, manufactured by Novo Nordisc Co., Ltd.
[4] Origin: Humicola sp., manufactured by Novo Nordisc Co., Ltd.
[5] Origin: Porcin pancreas, manufactured by Sigma Co., Ltd.
[6] Origin: Bovine pancreas, manufactured by Sigma Co., Ltd.
[7] Origin: Porcin liver, manufactured by Sigma Co., Ltd.
[8] Origin: Porcin pancreas, manufactured by Amano Pharmaceutical Co., Ltd.

As shown in Table 1, enzymes, which are not contained in the present invention, are used in each comparative example. Theses results show the reactivity (conversion) and stereoselectivity (optical purity) of comparative examples to be very inferior to those of examples. Even though the reactivity is good (as shown in comparative examples 4 and 7), the stereoselectivity is inferior to that of examples. On the other hand, enzyme derived from Candida genus in the above Examples 1–4 of the present invention, shows that the conversion is 16–76%, and the optical purity is 76–93% ee. From examples 1 and 2, in which the enzyme derived from *Candida antarctica* is used, it is particularly known that the conversion is 37–47%, the optical purity is 88–93% ee and both reactivity and stereoselectivity are excellent.

Reference example 1

Recemic endo-2-norborneol 700 g (6.42 mol), 2, 2, 2-trichloroethanol 770 g (3.11 mol), lipase (type II, origin:

Porcine pancrease, manufactured by Sigma Co., Ltd.) 560 g and diisopropylether 700 ml were mixed and the mixture was stirred for 290 hours at 25° C. Then, the conversion of the above racemic compound was 38%. The lipase was filtered from the reaction solution. The filtrate was concentrated under reduced pressure, and distilled under reduced pressure to obtain (R)-endo-2-caproyloxynorbornane (500 g, 2.38 mol, 37%). The resulting compound was subjected to a gas chromatograph and the optical purity of 83% ee was determined.

EXAMPLE 5

The (R)-endo-2-caproyloxynorbornane 5.0 g (23.8 mmol) having optical purity of 83% ee, lipase (Novozyme 435, origin: Candida antarctica, manufactured by Novo Nordisc) 2.0 g and water 50 ml were mixed. A 1N-NaOH aqueous solution was added dropwise to the mixture to adjust to pH 7 and stirred for 105 hours at 35° C. Then, the conversion of the above compound was 91%. The lipase was filtered from the reaction solution. The filtrate was extracted with ethyl acetate, the extract was dried over magnesium sulfate, and the solvent was distilled off under reduced pressure. The residue was subjected to a column chromatograph over silicagel to obtain (R)-endo-2-norborneol (2.33 g, 20.8 mmol, 87%). The resulting compound was subjected to the said gas chromatograph and the optical purity of 96% ee was determined.

EXAMPLE 6

Using the same procedure as in Example 5 except that pH of the reaction solution was 8, a mixture was prepared with stirring for 24 hours. Then, the conversion was 89%. The steps from the filteration of the lipase to silica gel chromatography were conducted as in Example 5, and (R)-endo-2-norborneol (2.36 g, 21.0 mmol, 89%) was obtained. The resulting product was subjected to the said gas chromatograph and the optical purity of 99% was determined.

EXAMPLE 7

The same lipase (SP 525) 0.25 g as used in Example 2 was dissolved in a 0.2M phosphoric buffer solution (pH 7.0) 40 ml containing 0.1M NaCl. The mixture and washed carrier (Trade name: Formylcellulofine, manufactured by CHISSO CORPORATION) 20 g were mixed and stirred for 30 minutes at room temperature. After adding sodium cyano borohydride 0.14 g, the mixture was stirred for 12 hours at room temperature. The supernatant fraction was filtered off, the residue was washed with a 0.2M tris-hydrochloric buffer solution (pH 7.2) 300 ml, a 0.2M tris-hydrochloric buffer solution (pH 7.2) 4 0 ml containing ethanol amine 0.24 g and sodium cyano borohydride 0.1 g was added, and the mixture was stirred for three hours at room temperature. The supernatant fraction was filtered off, the residue was washed with a 0.1M phosphoric buffer solution (pH 8.0) 150 ml and with a 0.07M phosphoric buffer solution (pH 7.0) 10 ml, and the immobilized lipase was obtained.

A mixture of the resulting immobilized lipase 20 g, racemic endo-2-propionyloxy norbornane 1.7 g (10 mmol) and a 0.7M phosphonic buffer solution (pH7.0) 30 ml was stirred for 50 hours at 35° C. Then, the conversion was 47%. The immobilized lipase was filtered and recovered from the reaction solution. The filtrate was extracted with ethyl acetate, the extract was dried over magnesium sulfate and the solvent was distilled under reduced pressure to obtain (R)-endo-2-norborneol (0.50 g, 4.5 mmol, 45%). After the residue was subjected to a gas chromatograph, the optical purity was 88% ee.

EXAMPLE 8

Using the immobilized lipase which was recovered in Example 7, racemic endo-2-propionyloxy norbornane was hydrolyzed as shown in Example (the second time), and the following operation was repeated up to 11 times. The results are shown in Table 2.

TABLE 2

|  | Reaction time (hr.) | Conversion (%) | Optical purity (% ee) |
|---|---|---|---|
| 2nd time | 94 | 48 | 88 |
| 3rd time | 45 | 46 | 89 |
| 4th time | 51 | 47 | 89 |
| 5th time | 62 | 49 | 87 |
| 6th time | 68 | 50 | 87 |
| 7th time | 52 | 45 | 89 |
| 8th time | 60 | 46 | 89 |
| 9th time | 60 | 45 | 89 |
| 10th time | 91 | 51 | 85 |
| 11th time | 91 | 50 | 85 |

As shown in Table 2, by using the immobilized lipase which was used in Example 7 and recovered in Example 8, the stereoselectively is good even if the lipase is repeatedly used, and the activity is difficult to lower. According to the method of the present invention, since expensive lipase can be repeatedly used, it is possible to efficiently prepare optically active endo-2-norborneols at low cost and in large quantities.

We claim:

1. A method for producing optically active endo-2-norborneols comprising asymmetrically hydrolysing racemic endo-2-acyloxynorbornane represented by formula (1):

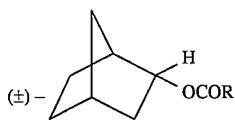
(1)

wherein R is straight or branched alkyl of 1–22 carbon atoms, alkenyl of 1–22 carbon atoms, cycloalkyl, aralkyl or aryl group with lipase derived from *Candida antartica*, obtaining a mixture of (R)-endo-2-norborneol represented by formula (2):

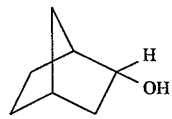
(2)

and (S)-endo-2-acyloxynorbornane represented by formula (3):

(3)

and isolating these compounds.

2. A method for producing optically active endo-2-norborneol as claimed in claim 1, wherein, in the compound represented by formula (1), R is selected from the group of ethyl, n-pentyl and henzyl.

3. A method for producing (R)-endo-2-norborneol comprising asymmetrically hydrolyzing endo-2-acyloxynorbornane having (R)-compound in excess, having an optical purity of 55–95% and represented by formula (5):

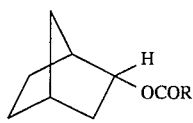
(5)

wherein R is straight or branched alkyl of 1–22 carbon atoms, alkenyl of 1–22 carbon atoms, cycloalkyl, aralkyl or aryl,
with the lipase derived from *Candida antarctica* to obtain (R)-endo-2-norborneol having optical purity of more than 95% ee.

4. A method as claimed in claim 3, wherein, in the compound represented by formula (5), R is selected from the group of ethyl, n-pentyl and benzyl.

5. A method as claimed in claim 1, wherein the lipase is immobilized on a carrier.

6. A method as claimed in claim 5, wherein the support for immobilizing the lipase is selected from the group consisting of porous polypropylene, porous acryl resin, polysaccharide gel modified with a formyl or epoxy group on the surface, acryl resin modified with a formyl or epoxy group on the surface, and polymer gel of a silicone type modified with a formyl or epoxy group.

7. A method as claimed in claim 2, wherein the lipase is immobilized on a carrier.

8. A method as claimed in claim 3, wherein the lipase is immobilized on a carrier.

9. A method as claimed in claim 4, wherein the lipase is immobilized on a carrier.

10. A method as claimed in claim 7, wherein the support for immobilizing the lipase is selected from the group consisting of porous polypropylene, porous acryl resin, polysaccharide gel modified with a formyl or epoxy group on the surface, acryl resin modified with a formyl or epoxy group on the surface, and polymer gel of a silicone type modified with a formyl or epoxy group.

11. A method as claimed in claim 8, wherein the support for immobilizing the lipase is selected from the group consisting of porous polypropylene, porous acryl resin, polysaccharide gel modified with a formyl or epoxy group on the surface, acryl resin modified with a formyl or epoxy group on the surface, and polymer gel of a silicone type modified with a formyl or epoxy group.

12. A method as claimed in claim 9, wherein the support for immobilizing the lipase is selected from the group consisting of porous polypropylene, porous acryl resin, polysaccharide gel modified with a formyl or epoxy group on the surface, acryl resin modified with a formyl or epoxy group on the surface, and polymer gel of a silicone type modified with a formyl or epoxy group.

* * * * *

UNITED STATES PATENT AND TRADEMARK OFFICE
CERTIFICATE OF CORRECTION

PATENT NO. : 5,604,120
DATED : February 18, 1997
INVENTOR(S) : HITOSHI YANO, TERUYO SUGIURA, YASUYUKI KOIZUME, and NAOYUKI YOSHIDA It is certified that error appears in the above-indentified patent and that said Letters Patent is hereby corrected as shown below:

Column 10, line 46 (in claim 1), correct the spelling of "antarctica".

Column 10, line 67 (in claim 2), correct the spelling of "benzyl".

Signed and Sealed this

Nineteenth Day of August, 1997

Attest:

BRUCE LEHMAN

Attesting Officer

Commissioner of Patents and Trademarks